(12) United States Patent
Vacher et al.

(10) Patent No.: US 7,982,054 B2
(45) Date of Patent: Jul. 19, 2011

(54) PROCESS FOR THE SYNTHESIS OF N-[3-[(2-METHOXYPHENYL] SULFANYL]-2-METHYLPROPYL]-3,4-DIHYDRO-2H-1,5-BENZOXATHIEPIN-3-AMINE

(75) Inventors: Bernard Vacher, Castres (FR); Yves Brunel, Marssac-sur-Tarn (FR); Jean-Louis Maurel, Burlats (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 316 days.

(21) Appl. No.: 12/312,440

(22) PCT Filed: Nov. 6, 2007

(86) PCT No.: PCT/FR2007/001831
§ 371 (c)(1),
(2), (4) Date: May 7, 2009

(87) PCT Pub. No.: WO2008/068403
PCT Pub. Date: Jun. 12, 2008

(65) Prior Publication Data
US 2009/0318709 A1    Dec. 24, 2009

(30) Foreign Application Priority Data
Nov. 8, 2006 (FR) ...................................... 06 09815

(51) Int. Cl.
*C07D 327/02* (2006.01)
*C07C 309/66* (2006.01)
*C07C 309/74* (2006.01)

(52) U.S. Cl. .......................................... 549/10; 558/44

(58) Field of Classification Search .................... 549/10; 558/44
See application file for complete search history.

(56) References Cited

FOREIGN PATENT DOCUMENTS
WO    2005/103027    11/2005

OTHER PUBLICATIONS
Written Opinion of The International Searching Authority For PCT/FR2008/001831 of Jul. 23, 2009.
International Search Report for PCT/FR2007/001831 of Oct. 3, 2008.
French Preliminary Search Report for FR 06/09815 of Jun. 4, 2007.

*Primary Examiner* — Bernard Dentz
(74) *Attorney, Agent, or Firm* — Hueschen and Sage

(57) ABSTRACT

The invention relates to a new process for the preparation of N-[3-[(2-methoxyphenyl)sulfanyl]-2-methylpropyl]-3,4-dihydro-2H-1,5-benzoxathiepin-3-amine.

7 Claims, No Drawings

PROCESS FOR THE SYNTHESIS OF N-[3-[(2-METHOXYPHENYL] SULFANYL]-2-METHYLPROPYL]-3,4-DIHYDRO-2H-1,5-BENZOXATHIEPIN-3-AMINE

The present invention relates to a new process for the preparation of the compound of formula (1)

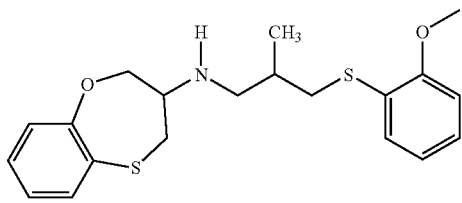

(1)

its addition salts with pharmaceutically acceptable inorganic acids or organic acids and hydrates of those addition salts, and also tautomeric forms thereof, enantiomers, mixtures of enantiomers and pure stereoisomers or stereoisomers in mixtures whether racemic or not.

The new process applies preferably to the compound (1) wherein the stereogenic carbon atom of the 3,4-dihydro-2H-1,5-benzoxathiepine fragment is of absolute configuration (R) and that of the propyl chain is of absolute configuration (S). The descriptors (R) and (S) used to specify the absolute configuration of the stereogenic atoms contained in the molecule of formula (1) are defined as in the Cahn-Ingold-Prelog priority rule (E. L. Eliel and S. H. Wilen Stereochemistry of Organic Compounds, John Wiley & Sons, Inc., chap. 5, 104-12, 1994).

In an especially advantageous embodiment of the invention, the selected stereoisomer of compound (1) is: (3R)-N-{(2S)-3-[(2-methoxyphenyl)sulfanyl]-2-methylpropyl}-3,4-dihydro-2H-1,5-benzoxathiepin-3-amine;

its addition salts with pharmaceutically acceptable inorganic acids or organic acids and hydrates of those addition salts. In the present invention, a stereoisomer is considered to be pure if it is associated with less than 1% of another stereoisomer or mixture of other stereoisomers (i.e., a diastereoisomeric excess of ≧98%, l'actualite chimique 2003, 11/12, 10-4).

The compound of formula (1) is described in Patent Application WO 02/081464, where it is claimed as being useful in the treatment of stable angina, unstable angina, heart failure, long QT syndrome of congenital origin, myocardial infarction and disorders of cardiac rhythm. In that Application, the compound of formula (1) is obtained by reductive amination between the compound of formula (2) and the aldehyde of formula (5) in accordance with the following Scheme I:

Scheme I

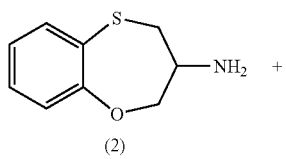

(2)

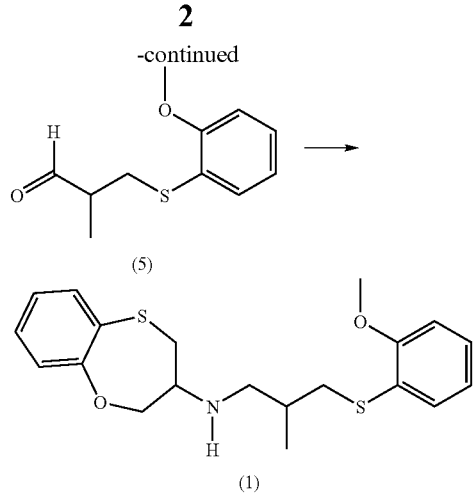

However, this reductive amination reaction is problematic because of the chemical and stereochemical instability of the aldehyde of formula (5). In addition, because of the nature of some of the reagents used and also that of some of the sub-products formed, this procedure is difficult to perform on an industrial level.

In the synthesis process described in the Application WO 05/103027, the compound of formula (1) is prepared in accordance with Scheme II by reduction of the amide of formula (6), which is chemically and stereochemically stable. The advantage of that process lies essentially in the fact that it is robust, can be performed on an industrial level and can therefore be potentially used in the production of large quantities of compound (1), unlike the process shown in WO 02/081464.

Scheme II

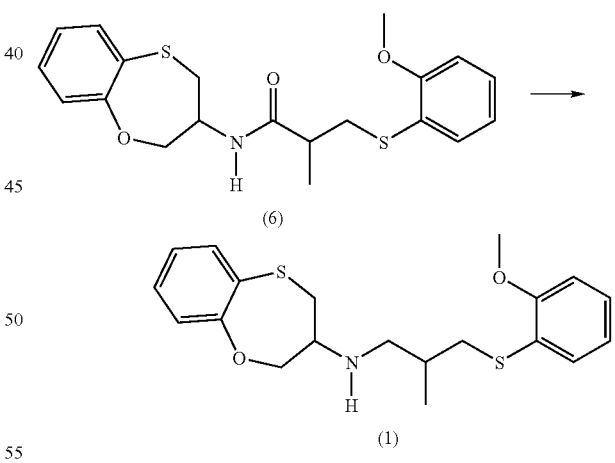

However, although that process can be performed on an industrial level, it does have two major disadvantages limiting, or considerably complicating, the exploitation thereof:

The final step in the WO 05/103027 process involves the reduction of an amide function to the corresponding amine by means of a borane complex ($BH_3.THF$) in the hot state. Under the synthesis conditions required to bring about said reduction reaction, boron hydride ($BH_3$) can give rise to diborane $B_2H_6$, which is toxic, extremely flammable and explosive (INRS, FT No. 188, 1987). Because of the potential risks of toxic effects, fire and explosion due to the possible formation of $B_2H_6$, strict preventative and protective measures must be put in place when handling the $BH_3.THF$ complex, which considerably complicates exploitation of the process.

Moreover, it has been found that reduction of the amide (6) to the amine (1) by means of reducing agents other than a borane complex (i.e. which cannot give rise to $B_2H_6$) is not satisfactory.

Another limiting factor comes from the fact that, in the process described in WO 05/103027, synthesis of the intermediate compound (6) involves the use, as starting material, of methyl (R)-3-hydroxy-2-methyl-propanoate [72657-23-9], which is difficult to obtain on an industrial scale.

Perfecting a synthesis process that can be performed industrially without the disadvantages described hereinbefore is accordingly necessary for the preparation of medicaments that are useful in the treatment of stable angina, unstable angina, heart failure, long QT syndrome of congenital origin, myocardial infarction and disorders of cardiac rhythm.

The present invention accordingly relates to a new process for the synthesis of compound (1) which is free of the limitations described hereinbefore.

The process of the invention, unlike that shown in WO 05/103027, thus no longer involves reduction of an amide function, which reduction requires using a reducing agent of the borane complex type. The safety of the new process is considerably increased as a result.

Another major improvement of the process of the invention lies in the fact that a compound of the (S)-3-halogeno-2-methylpropanol type is used as starting material, which is more readily obtainable on a large scale than the methyl (R)-3-hydroxy-2-methyl-propanoate used in the process described in WO 05/103027.

Accordingly, in terms of the safety of exploitation and in economic terms, the process of the invention has marked advantages compared to the process described in Patent Application WO 05/103027.

A first aspect of the invention accordingly relates to improvement of the process for the synthesis of the compound of formula (1)

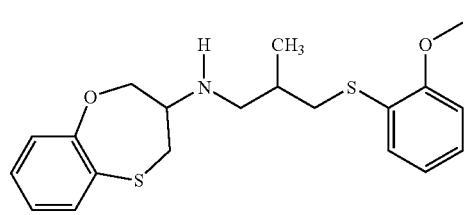
(1)

This compound is obtained by condensation of the compounds of formulae (2) and (3)

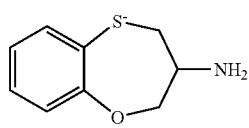
(2)

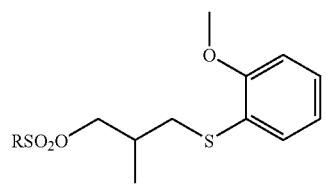
(3)

wherein the radical R represents a methyl group or, preferably, a 4-methylphenyl group, in accordance with Scheme III.

Scheme III

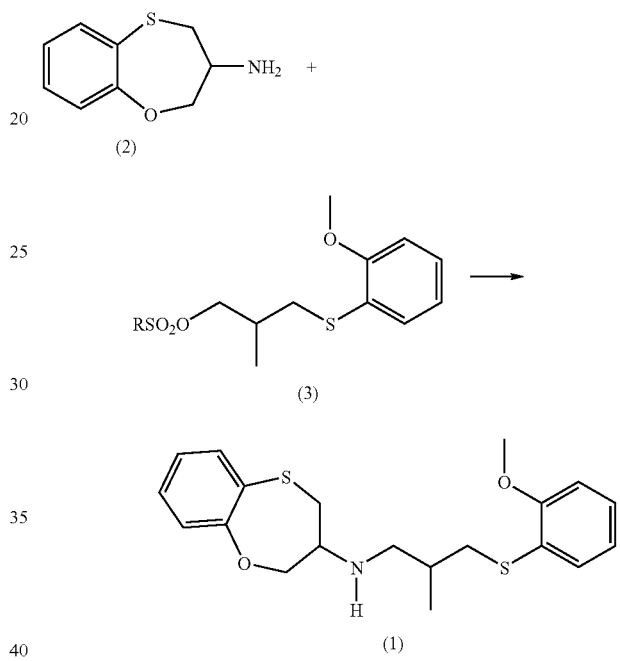

The preferred stereoisomer of the compounds of formulae (1), (2) and (3) is, in all cases, that wherein the stereogenic carbon atoms of the 3,4-dihydro-2H-1,5-benzoxathiepine fragment and of the chain are of absolute configuration (R) and (S), respectively.

In accordance with the new process of the invention, the amine (2) reacts under heat, preferably from 100 to 200° C., with a compound of formula (3), preferably the tosylate, in the presence of a base, for example a non-nucleophilic nitrogen-containing base such as diisopropylethylamine or triethylamine, in an inert solvent such as toluene or xylene.

Replacement of a tosylate group by a primary amine is a well-known reaction in organic chemistry, for example Organic Process Research & development 2005, 9(3), 314. However, in unexpected manner, the reaction of the amine (2) with the tosylate (3) has been found to be remarkably efficient. In fact, in the course of said reaction the formation neither of product resulting from dialkylation of the amine (2) by the tosylate (3) nor of secondary products originating from the elimination of p-toluenesulfonic acid from (3) has been observed. Moreover, under the reaction conditions there is no substantial racemisation, whether as regards the intermediates (2) and (3) or as regards the product (1) formed. It follows therefrom that the product of formula (1) is obtained in satisfactory yield and with satisfactory stereochemical purity.

From a technical point of view, carrying out the reaction and processing of the reaction mixture are simple to perform. The process of the invention is accordingly especially suitable for the production of large quantities of the compound of formula (1).

A second aspect of the invention comprises a process for the synthesis of the new intermediate of formula (3)

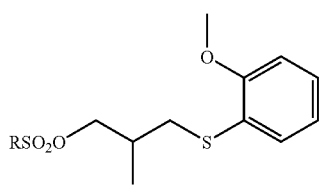
(3)

in accordance with Scheme IV

Scheme IV

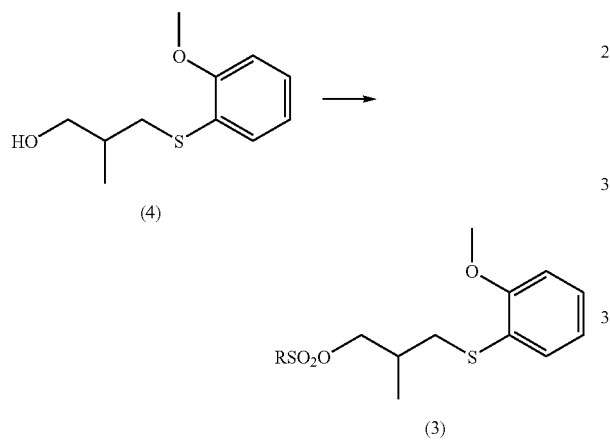

wherein the compound of formula (4): 3-(2-methoxyphenyl-sulfonyl)-2-methylpropanol

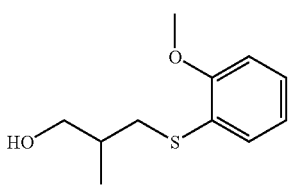
(4)

is treated with methanesulfonyl chloride or para-toluenesulfonyl chloride, in the presence of an organic or inorganic base such as, for example, pyridine, triethylamine, potassium carbonate or ground anhydrous potassium hydroxide, to yield the compound of formula (3). The alcohol function of 3-(methoxyphenyl)sulfanyl-2-methylpropanol of formula (4) is thus activated, preferably in the form of a tosylate, to yield the new compound of formula (3). The preferred enantiomer of compounds of formula (3) is that wherein the stereogenic carbon atom is of absolute configuration (S).

The compound of formula (3) is subsequently condensed with the amine (2) to yield compound (1) (Scheme III).

Another aspect of the invention relates to the intermediate compound of general formula (3)

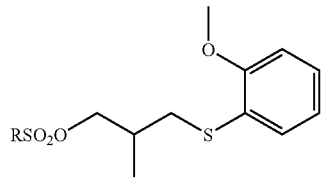
(3)

wherein the radical R is a methyl or, preferably, 4-methylphenyl group.

More especially, the invention relates to the intermediate compound of general formula (3) as described hereinbefore wherein the stereogenic carbon atom of the propyl chain is of absolute configuration (S).

The following Examples illustrate the invention without however limiting the scope thereof.

EXAMPLE 1

(S)-3-(2-methoxyphenyl)sulfanyl-2-methylpropanol 4-methylbenzenesulfonate (3)

10 ml of methylene chloride, 2 g (9.4 mmol) of (S)-3-(2-methoxyphenylsulfanyl)-2-methylpropanol, 2 g (10.5 mmol) of para-toluenesulfonyl chloride and 115 mg (0.94 mmol) of 4-dimethylaminopyridine are introduced into a three-necked flask under an inert atmosphere and 1.2 g (12.1 mmol) of triethylamine are then added dropwise. After stirring for 2 hours at ambient temperature, 10 ml of demineralised water are added. The pH is adjusted to 6.5 by adding 2N hydrochloric acid. The phases are separated and then the organic phase is washed with 10 ml of demineralised water. The organic phase is concentrated under reduced pressure. The yellow oil obtained (3.2 g) is taken up in a mixture of methylene chloride (4.8 ml) and 19.2 ml of isopropyl ether. The precipitate obtained is filtered off and then washed twice with 10 ml of isopropyl ether and dried at 40° C. under reduced pressure. The title product (3) is obtained in the form of a white powder 2.6 g (75%).

Rf=0.56 (heptane/AcOEt: 60/40; Merck 254 silica)
m.p.=86-87° C.
$^1$H NMR (CDCl$_3$) δ: 1.03 (d, 3H, J=7.0 Hz); 2.02 (m, 1H); 2.43 (s, 3H); 2.71 (dd, 1H, J=6.8 Hz, J=13.0 Hz); 2.89 (dd, 1H, J=6.7 Hz, J=13.0 Hz); 3.87 (s, 3H); 4.01 (d, 2H, J=5.6 Hz); 6.84 (d, 1H, J=7.6 Hz); 6.88 (dd, 1H, J=7.1 Hz, J=7.6 Hz); 7.10 (d, 1H, J=7.6 Hz); 7.18 (dd, 1H, J=7.1 Hz, J=7.6 Hz); 7.32 (d, 2H, J=8.1 Hz); 7.77 (d, 2H, J=8.1 Hz).
$^{13}$C NMR (CDCl$_3$) δ: 16.26; 21.62; 32.95; 35.14; 55.73; 73.37; 110.60; 121.02; 123.63; 127.62; 127.88 (2C); 129.81 (2C); 130.21; 132.88; 144.70; 157.64.
HPLC, chiralcel OD column (250×4.6 mm), eluant (hexane/ethanol/diethylamine: 97/3/0.1), 1 ml/min, Rt (S)=21.02 min; Rt (R)=19.77 min. Chiral purity (S isomer) determined using the area under the curve (99%).
MS (APCI+) m/z: 367 (M+H), 195 (M-TsO).

EXAMPLE 2

(3R)-N-{(2S)-3-[(2-methoxyphenyl)sulfanyl]-2-methylpropyl}-3,4-dihydro-2H-1,5-benzoxathiepin-3-amine (1)

6.5 g (35.9 mmol) of (R)-3,4-dihydro-2H-1,5-benzoxathiepin-3-amine and 11 g (30 mmol) of (S)-3-(2-methoxyphenyl-sulfanyl)-2-methylpropyl 4-methylbenzenesulfonate in 33 ml of toluene are introduced into a three-necked flask under an inert atmosphere. 6 g (60 mmol) of triethylamine are added and then the reaction mixture is heated with stirring at 105° C. for 24 hours. After returning to ambient temperature, 33 ml of toluene are added. The organic phase is washed twice with 66 ml of demineralised water and is then decolourised by stirring for one hour in the presence of 2 g of Black CXV. After concentrating under reduced pressure, driving-off with 33 ml of ethanol 100 is carried out. The title product is obtained in the form of a yellow oil (8.85 g; 79%).

Rf=0.53 (heptane/AcOEt: 60/40; Merck 254 silica) 8.85 g (23.5 mmol) of compound (1) are introduced into 53 ml of a mixture of ethanol 100/methyl tert-butyl ether (2/4 v/v). A solution of hydrobromic acid 62% (3 g; 23.5 mmol) is poured slowly into the solution of amine at ambient temperature and then, after stirring for two hours at ambient temperature, the solid obtained is filtered off and washed three times with 15 ml of methyl tert-butyl ether. Drying for 12 hours at 50° C. yields 7.3 g (68%) of the hydrobromide of compound (1).

m.p.=129-131° C.;

$^1$H NMR (DMSO-d$_6$) ? 1.12 (d, 3H), 2.19 (m, 1H), 2.82 (dd, 1H), 3.05 (lm, 1H), 3.12 (dd, 1H), 3.23 (lm, 1H), 3.32 (m, 2H), 3.82 (s, 3H), 3.90 (ls, 1H), 4.39 (dd, 1H), 4.52 (dd, 1H), 6.98 (m, 2H), 7.07 (m, 2H), 7.23 (m, 3H), 7.40 (dd, 1H), 8.88 (ls, exchangeable 2H);

HPLC, chiralcel OJ column (250×4.6 mm), eluant (methanol/ethanol/diethylamine: 50/50 0.1) 1 ml/min, Rt (R,S)= 24.37 min; Rt (R,R)=16.80 min; Rt (S,S)=19.79 min; Rt (S,R)=15.05 min). Chiral purity (R,S isomer) determined by the percentage area under the curve (98%).

The invention claimed is:

1. Process for the preparation of N-[3-[(2-methoxyphenyl) sulfanyl]-2-methylpropyl]-3,4-dihydro-2H-1,5-benzoxathiepin-3-amine of general formula (1)

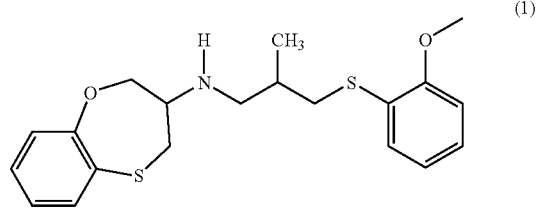

comprising condensation of the intermediates of formulae (2) and (3)

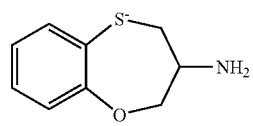

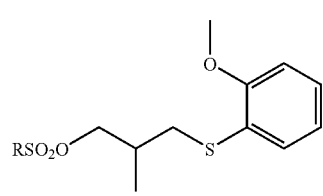

wherein the radical R is a methyl group or a 4-methylphenyl group.

2. A process of claim 1, wherein the intermediates of formula (3), where R is a methyl group or a 4-methylphenyl group,

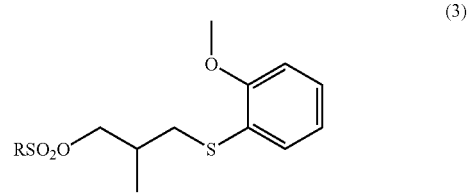

are prepared by the treatment of 3-[(2-methoxyphenyl) sulfanyl]-2-methylpropanol of formula (4)

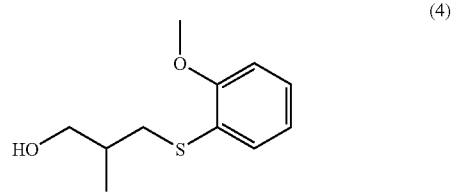

with an appropriate sulfonyl chloride to yield an intermediate of formula (3).

3. A process of claim 1, wherein intermediates of formula (3) are used in the preparation of compounds of formula (1).

4. A process for the preparation of N-[3-[(2-methoxyphenyl)sulfanyl]-2-methylpropyl]-3,4-dihydro-2H-1,5-benzoxathiepin-3-amine of formula (1) of claim 1, wherein the compound of formula (1) is of absolute configuration (R) at the stereogenic carbon atom of the 3,4-dihydro-2H-1,5-benzoxathiepine fragment and is of absolute configuration (S) at the stereogenic carbon atom of the propyl chain.

5. A process for the preparation of N-[3-[(2-methoxyphenyl)sulfanyl]-2-methylpropyl]-3,4-dihydro-2H-1,5-benzoxathiepin-3-amine of formula (1) of claim 1, wherein the stereogenic carbon atom of the intermediate of general formula (3) is of absolute configuration (S).

6. An intermediate compound of formula (3),

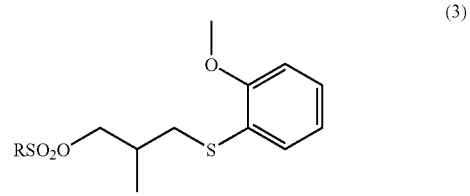

wherein the radical R is a methyl group or a 4-methylphenyl group.

7. The intermediate compound of claim 6 having the general formula (3), wherein the stereogenic carbon atom of the propyl chain is of absolute configuration (S).

* * * * *